(12) United States Patent
Asotra et al.

(10) Patent No.: US 7,799,331 B2
(45) Date of Patent: Sep. 21, 2010

(54) ORAL SUSPENSION OF PREDNISOLONE ACETATE

(75) Inventors: Satish Asotra, Brampton (CA); Shen Gao, Botton (CA); Avraham Yacobi, Englewood, NJ (US)

(73) Assignee: Taro Pharmaceutical North America, Inc., Grand Cayman (KY)

( * ) Notice: Subject to any disclaimer, the term of this patent is extended or adjusted under 35 U.S.C. 154(b) by 821 days.

(21) Appl. No.: 11/457,197

(22) Filed: Jul. 13, 2006

(65) Prior Publication Data

US 2007/0031459 A1 Feb. 8, 2007

Related U.S. Application Data

(60) Provisional application No. 60/705,370, filed on Aug. 4, 2005.

(51) Int. Cl.
*A61K 31/57* (2006.01)
*A61K 9/00* (2006.01)
*A61K 9/14* (2006.01)

(52) U.S. Cl. .................. 424/400; 514/178; 424/489

(58) Field of Classification Search .................. None
See application file for complete search history.

(56) References Cited

U.S. PATENT DOCUMENTS

| | | | | |
|---|---|---|---|---|
| 4,265,823 A * | 5/1981 | Nobile | ..................... | 552/504 |
| 4,448,774 A | 5/1984 | Clemente et al. | | |
| 5,145,675 A * | 9/1992 | Won | ..................... | 424/78.31 |
| 5,525,605 A * | 6/1996 | Omura | ..................... | 514/259.41 |
| 5,763,449 A | 6/1998 | Anaebonam et al. | | |
| 5,811,388 A * | 9/1998 | Friend et al. | ..................... | 514/2 |
| 5,881,926 A | 3/1999 | Ross | | |
| 5,962,461 A * | 10/1999 | Anaebonam et al. | ..................... | 514/275 |
| 6,071,523 A | 6/2000 | Mehta | | |
| 6,102,254 A | 8/2000 | Ross | | |
| 6,355,258 B1 | 3/2002 | Mehta et al. | | |
| 6,399,079 B1 | 6/2002 | Mehta et al. | | |
| 6,656,482 B2 | 12/2003 | Mehta et al. | | |
| 6,969,706 B1 * | 11/2005 | Chang et al. | ..................... | 514/60 |
| 2002/0137728 A1 * | 9/2002 | Montgomery | ..................... | 514/99 |
| 2003/0119786 A1 * | 6/2003 | Keith et al. | ..................... | 514/81 |
| 2005/0020551 A1 * | 1/2005 | Bodor | ..................... | 514/177 |
| 2005/0153946 A1 | 7/2005 | Hirsh et al. | | |

FOREIGN PATENT DOCUMENTS

WO WO 03/030823 4/2003

OTHER PUBLICATIONS

International Search Report issued in PCT Application PCT/US06/30140, mailed on Jul. 27, 2007.
International Preliminary Report on Patentability issued Feb. 5, 2008 for related PCT/US2008/030140.

* cited by examiner

*Primary Examiner*—Robert A Wax
*Assistant Examiner*—Danah Al-Awadi
(74) *Attorney, Agent, or Firm*—Venable LLP; Zayd Alathari; Thomas F. Barry

(57) ABSTRACT

The present invention relates to novel oral suspension formulation comprising prednisolone acetate, a pharmaceutically acceptable vehicle and a thickening agent. The present invention further provides a method of treating patients in need of prednisolone with the novel formulation.

32 Claims, No Drawings

ORAL SUSPENSION OF PREDNISOLONE ACETATE

CROSS REFERENCE TO RELATED APPLICATION

This application claims the benefit under 35 U.S.C. §119 (e) of the U.S. Provisional Application No. 60/705,370 filed Aug. 4, 2005, the disclosure of which is incorporated by reference in its entirety herein.

BACKGROUND OF THE INVENTION

The invention relates to a pharmaceutical formulation for oral administration comprising an effective amount of prednisolone acetate in a pharmaceutically acceptable, aqueous, suspension-stabilizing vehicle.

Corticosteroids are used to treat patients with inflammatory and immune diseases. Prednisolone is a corticosteroid that has been formulated into capsules, tablets and liquid preparations for oral delivery. The base form of prednisolone and the salt form, prednisolone sodium phosphate, are commercially available in oral liquid formulations. However, the bitter taste of the commercial compositions is described extensively in the medical literature and contributes to poor patient compliance with medical instructions for the use of the drug. U.S. Pat. No. 4,448,774 describes aqueous solutions comprising a steroid selected from the group of prednisolone, prednisolone sodium phosphate, prednisone and methyl prednisolone. The solution described in the patent is described as being preferable to previously known formulations because no alcoholic solvent is required and it is not a suspension. Suspensions of prednisolone are reported to be problematic because they are not stable and over time the active agent settles out of the formulation and gives variable dosage amounts. U.S. Pat. No. 5,763,449 describes the use of a combination of three well known taste masking agents to achieve a pleasant tasting liquid pharmaceutical composition. Prednisolone and prednisolone sodium phosphate are disclosed as bitter tasting drugs that may be used in the formulation.

Another form of prednisolone, prednisolone acetate, is commonly used for medicinal purposes. However, because of its poor aqueous solubility, prednisolone acetate is used in topical, parenteral and opthamalogical formulations, not oral formulations. The use of the acetate form could provide a taste advantage because it is insoluble in the aqueous environment of the mouth, and therefore prevents the interaction of the bitter-tasting molecules of the prednisolone with the taste buds.

The present disclosure is to a novel, organoleptic, oral, liquid suspension of prednisolone acetate that is an improvement over previously disclosed and commercialized oral prednisolone dosage forms.

SUMMARY OF THE INVENTION

The present invention is to a pharmaceutical composition for oral delivery comprising a pharmaceutically effective amount of prednisolone acetate, pharmaceutically acceptable vehicle and a thickening agent. The present composition contains between about 0.5 mg/mL to about 7 mg/mL of prednisolone acetate. More preferably the concentration of prednisolone acetate is between about 1 mg/mL to about 5 mg/mL. The most preferred compositions of the present invention will deliver 5 mg/5 mL prednisolone acetate or 15 mg/5 mL prednisolone acetate.

The inventive formulation has prednisolone acetate dispersed in an oral formulation comprising a vehicle and a thickening agent. The aqueous vehicle may be comprised of glycerin, and the preferred thickening agent is carbomer.

The prednisolone acetate of the present invention is within a fine range of particle size. The median particle size of the prednisolone acetate is between about 1 μm to 30 μm, particularly between about 5 μm to 10 μm, and more particularly between 6 μm to 8 μm. Ninety percent of the prednisolone acetate in the inventive composition has a median particle size of greater than 1 μm and less than 30 μm.

The inventive composition further comprises pharmaceutically acceptable excipients. The excipients include wetting agents, spreading agents, stabilizers, sweeteners and flavoring agents. The inventive composition is organoleptically pleasing.

The novel formulation has a pH of between about 4.0 to about 5.9, more preferably of between about 4.6 to about 5.4, most preferably 4.8 to 5.2.

The inventive composition is comprised of from about 29 to about 64% water (w/w), up to about 50% glycerin (w/w), up to about 20% sorbitol (w/w), up to about 10% propylene glycol (w/w), up to about 3% surfactant (w/w) and up to about 1% of a thickening agent (w/w).

The pharmaceutical composition of the invention comprises the following ingredients a) 0.1% poloxamer 188; b) 50% glycerin; c) 5% sorbitol crystalline; d) 5% propylene glycol; e) 0.065% disodium edetate; f) 0.2% sucralose; g) 0.44% carbomer; h) 0.04% butylparaben; and i) sodium hydroxide to a pH of between about 4.8 to about 5.2.

The inventive formulation may be used to treat a patient in need of an effective amount of the active pharmaceutical vehicle, prednisolone.

Among the medical conditions that may be treated by the formulation of the present invention are endocrine disorders, rheumatic disorders, collagen diseases, dermatologic diseases, allergic states, respiratory diseases, hemaologic disorders, neoplastic diseases, edema, gastrointestinal diseases or nervous diseases using an effective amount of the orally delivered prednisolone acetate composition.

DETAILED DESCRIPTION OF THE INVENTION

In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled in the art in light of the above teachings. Each reference cited herein is incorporated by reference as if each were individually incorporated by reference.

The formulation of the present invention is a palatable, oral formulation of prednisolone acetate. Prednisolone acetate has been used in ophthalmic and parenteral medicinal products, but has not previously been used in oral liquid preparations. Prednisolone acetate is practically insoluble in water. The low solubility presents a formulary challenge during product development of an aqueous liquid oral preparation. However, the use of the acetate form provides a taste advantage because the active does not dissolve in the aqueous environment of the mouth, and therefore prevents the interaction of the bitter-tasting molecules of the prednisolone with the taste buds.

The present invention is an aqueous suspension having a thickening component and a vehicle, or carrier, component and may include other pharmaceutically acceptable excipients. The vehicle is pharmaceutically acceptable, aqueous and suspension-stabilizing. Prednisolone acetate is evenly dispersed in the semi-solid aqueous vehicle. The suspension has a homogeneity so that the active ingredient is uniformly dispersed but undissovled in the vehicle. The formulation consists of mutually compatible components at room temperature. The suspension has a crystalline stability in that the prednisolone particles stay within a target particle size range over time.

The vehicle component serves as the external phase of the suspensions. The vehicle may be comprised of water, glycerin, propylene glycol and mixtures thereof. The vehicle component may contain glycerin up to about 50%. The vehicle may also comprise propylene glycol up to about 20% or from about 3% to about 10%. Purified water comprises the bulk of the vehicle component comprising from about 29% to about 64% of the formulation.

Purified water makes up the bulk of the vehicle component, comprising from about 29% to 64% (w/w) of the formulation. Water concentration can be less than about 50% (w/w) or even less than about 43% (w/w).

Thickening agents are pharmaceutically acceptable excipients that add a desired viscosity and flow to a formulation. Carbomers are synthetic high molecular weight polymers of acrylic acid. In one embodiment, carbomer 943P (Carbopol 974P) has been found to be a suitable thickening, or gelling agent, providing good sensory appeal and texture. The rheology of the carbomer provides for a high yield value, low shear thinning quality, in non-thixotropic liquid formulations.

The viscosity of the carbomer gel is pH dependent. Carbomer gels exhibit maximum viscosity at about pH 7.0. More acidic or basic pH's will cause the carbomer to lose viscosity. However, prednisolone acetate is most stable at slightly acidic pH's, and will degrade to undesirable breakdown products at the higher pH. At neutral pH's, prednisolone acetate will undergo oxidation and hydrolysis and form undesirable and less active degradation products. At a pH of 4.6 to 5.4, prednisolone acetate is stable in the formulation and the carbomer may retain its viscosity. The carbomer comprises up to about 1% (w/w) of the inventive formulation. In particular, we have found that the carbomer of the inventive formulation should be between about 0.40% to about 0.50%, more particularly, about 0.40% to about 0.48%.

The oral formulation of prednisolone acetate is a spill-resistant formulation. Spill resistant oral formulations are more extensively described in, for example, U.S. Pat. Nos. 6,071,523, and 6,102,254, herein incorporated by reference.

The pharmaceutical suspension comprising of the invention has prednisolone acetate uniformly dispersed in an aqueous vehicle, the active ingredient remaining in suspension without agitation during the product shelf-life. The shelf life may be up to about six, twelve, eighteen, twenty-four months, thirty months, or thirty-six months. The suspension has antimicrobial activity, is pharmaceutically effective and meets applicable regulatory requirements as would be understood by a person of ordinary skill. The viscosity may be about 5,000 to about 15,000 cps, about 5,000 to about 14,800 cps, about 9,000 to about 11,000 cps, or about 9,500 to about 10,500 cps. In inventive pharmaceutical suspensions there is no crystalline growth during a heat-cool study for three days at a temperature range of about 8° C. to about 45° C. The active ingredient particles may be crystals that neither dissolve or grow substantially when the sample is heated e.g. to 45° C. and cooled to room temperature repeatedly.

The formulation is dosed by volume, and specific gravity values were used to estimate the prednisolone acetate concentration in the composition. The 5 mg/mL dose was calculated, based on specific gravity to be 0.097% (w/w), which is equivalent to 0.087% (w/w) of the prednisolone base form. The 15 mg/mL dose was calculated to be about 0.293% (w/w), which is equivalent to 0.262% of prednisolone base form.

The particle size of the active pharmaceutical ingredient may have important effects on the bioavailability of a formulation. Smaller particle sizes have increased surface area and will dissolve faster than larger particles. However, decreasing the particle size may cause some agglomeration of the particles, and the increased surface area can result in faster degradation of the compound due to oxidation and hydrolysis. In the inventive formulation, a fine particle size was found to achieve the desired bioavailabilty. The prednisolone to acetate of the inventive formulation has a median particle size of approximately from about 1 µm to about 30 µm, more preferably about 5 µm to about 20 µm, most preferably from about 6 µm to about 8 µm. The particle size may be achieved using such methods air-jet milling, ball milling, mortar milling or any other method known in the art for decreasing particle size. For example, the prednisolone acetate particles of the disclosed formulation were micronized using a stainless steel, air-jet mill with a grinding chamber diameter of four inches (Sturtevant, Hanover, Mass., U.S.A., model no. SDM-4.)

The size of the particles may be measured using a light scattering device, sedimentation methods, centrifugal force measurements, or any method known to one skilled in the art. By means of an example, the Matersizer 2000 manufactured by Malvern Instruments, Ltd., Malvern U.K., may be used to measure the particle size.

Pharmaceutical excipients are pharmaceutically acceptable ingredients that are essential constituents of virtually all pharmaceutical products. Excipients serve many purposes in the formulation process. The inventive pharmaceutical suspensions may comprise at least one additional component selected from the group consisting of excipients, surface active agents, dispersing agents, sweetening agents, flavoring agents, coloring agents, preservatives, oily vehicles, solvents, suspending agents, dispersing agents, wetting agents, emulsifying agents, demulcents, buffers, salts, spreading agents, antioxidants, antibiotics, antifungal agents and stabilizing agents.

Spreading agents may be added to the vehicle component. Polyols, such as malitol, mannitol, polyethylene glycol and sorbitol may be added to the vehicle components to adjust the spreadability in the spoon bowl upon pouring. The present embodiment may contain sorbitol, in a concentration of less than 5%.

The suspensions of the present invention may also contain Edetate Disodium (EDTA). EDTA is a chelating agent that forms a stable water-soluble complex with alkaline earth and heavy metal ions. It is useful as an antioxidant synergist, sequestering metal ions that might otherwise catalyze autoxidation reactions. EDTA may also have synergistic effects as an antimicrobial when used in combination with other preservatives (Handbook of Pharmaceutical Excipients $4^{th}$ Ed.).

The suspension formulations may require a crystal conditioning surfactant, i.e. a wetting agent. The hydrophobic properties of prednisolone acetate may benefit from a wetting agent to disperse the steroid in the formulation. A concentration of from about 0.05% to about 0.5% poloxamer 188 was found to be effective at wetting the prednisolone acetate without excessive foaming and dispersion of the suspension.

The present formulation is an improvement over previously described prednisolone suspensions because the ingredient remains suspended indefinitely, without agitation; that is without stirring or shaking. The dispensed dose is always uniform over the shelf life of the product. The formulation of the invention can not be shaken easily, so the particles remain suspended without shaking.

The suspension has antimicrobial activity. Propylparaben (up to about 0.04%) and butylparaben (0.018% to about 0.18%) are suitable. Other antimicrobial excipients may also be used. These suspensions are alcohol-free.

The organoleptic ingredients improve the taste and appearance and do not negatively affect the suspension stability. The organoleptic agents in the following examples include coloring and flavoring agents, sweeteners and masking agents.

Mutual compatibility of the components means that the components do not separate in preparation and storage for up to the equivalent of two years at room temperature (as indicated by three month intervals of accelerated stability testing at 40° centigrade and at 75% relative humidity). Storage stability means that the materials do not lose their desirable properties during storage for the same period. Preferred compositions do not exhibit a drop in viscosity of more than 50% or an increase in viscosity of more than 100% during that period.

The following examples further illustrate the invention, but should not be construed as limiting the invention in any manner.

EXAMPLE 1

The prednisolone acetate oral suspension was formulated to contain the following ingredients:

TABLE I

Composition of Oral Prednisolone Acetate Suspension

| INGREDIENTS | 5 mg/5 mL (w/w %) | 15 mg/mL |
|---|---|---|
| Prednisolone Acetate | 0.097 | 0.293 |
| Poloxamer 188 | 0.1 | 0.1 |
| Glycerin | 50 | 50 |
| Sorbitol Crystalline | 5 | 5 |
| Propylene Glycol | 5 | 5 |
| Edetate Disodium | 0.065 | 0.065 |
| Sucralose | 0.2 | 0.2 |
| Artificial Cherry Flavor | 0.15 | 0.15 |
| Bell Flavor Masking Agent | 0.2 | 0.2 |
| Carbomer 934 | 0.44 | 0.44 |
| Butylparaben | 0.04 | 0.04 |
| Purified water | to 100% | to 100% |
| NaOH | pH 4.6-5.4 | pH 4.6-5.4 |

EXAMPLE 2

Comparison of Different Prednisolone Actives for Sensory

Evaluation: A small sample of volunteers compared the different formulations of prednisolone for taste and flavor. Results are given in Table 2.

TABLE 2

Sensory Perception following different samples of Prednisolone Formulations

| Product Description | Initial Taste | After Taste |
|---|---|---|
| Commercially Available Prednisolone 5 mg/5 ml | Slightly sweet, intense wild cherry | Persistent, very bitter |
| Commercially Available Prednisolone sodium phosphate 5 mg./5 ml | Moderately sweet, mild raspberry | Delayed moderately bitter unpleasant taste persists for long time |
| Taro Prednisolone Phosphate Experimental Syrup 5 mg/5 mL | Pleasantly sweet, cherry flavored | Delayed slightly bitter, Intensity increases with time |
| Prednisolone Acetate Suspension 5 mg/mL | Pleasantly sweet, cherry flavored | No bitterness perceived |

EXAMPLE 3 pH Screen Stability

Stability testing was performed on 1.0 kg portions of a 5.0 kg experimental batch of 5 mg/5 mL prednisolone acetate. NaOH was added to the portions to give various pH values (Batch A-E) and packaged in 4 ounce amber PETG bottles. The samples were left at the environmentally stressed conditions of 40° centigrade or 50° centigrade for one month. HPLC methods were used to measure the percent of prednisolone acetate retained in the bottle. The control sample used was a 5 mg/5 mL prednisolone acetate suspension exposed at room temperature and sampled after 4 months. The data is summarized in Table 3.

As demonstrated by the results shown in Table 3, in the pH range of 5.0 to 6.2, the micronized prednisolone acetate is more stable at the lower pH values.

TABLE 3

Stability of Prednisolone Acetate Oral Suspension (varying pH)

| Batch No. | pH | (%)Prednisolone Acetate[1] (RT) | (%)Prednisolone Acetate[1] (40° C.) | (%)Prednisolone Acetate[1] (50° C.) |
|---|---|---|---|---|
| A | 5.02 | 96.7 | 96.7 | 95.2 |
| B | 5.39 | 96.1 | 96.1 | 93.0 |
| C | 5.71 | 95.4 | 95.4 | 81.7 |
| D | 5.90 | 92.8 | 92.8 | 44.3 |
| E | 6.22 | 87.3 | 87.3 | 67.4 |

EXAMPLE 4

Suspension Dissolution

Dissolution tests are a qualitative tool that provides information about the biological availability of a drug formulation. Experimentally, suspension formulations are considered to disintegrate equivalently to tablet formulations, therefore dissolution testing is done comparing suspensions to tablets. A standard dissolution test (USP Apparatus 2 (paddle)) was followed to compare the prednisolone acetate suspension to a commercially available 5 mg tablet of prednicolone. As shown in FIG. 1, the dissolution curves of the suspensions were very similar to the dissolution curve for the tablet following a 15 minute period.

TABLE 4

Dissolution of Prednisolone Acetate Suspensions v. Prednisolone Tablets

| TIME | Prednisolone Acetate Suspension | | Prednisolone Tablets |
|---|---|---|---|
| | 15 mg/5 ml | 5 mg/5 ml | 5 mg |
| 5 | 48 | 45 | 69 |
| 15 | 85 | 82 | 93 |
| 30 | 95 | 93 | 96 |
| 45 | 97 | 95 | 98 |
| 60 | 97 | 96 | 98 |

EXAMPLE 5

Twenty three volunteers (male and female non- or exsmokers) were orally administered a single 5 my dose of prednisolone in the morning after a ten hour overnight fast. The study design was a randomized, 6-sequence, 3-period, crossover design. Either 5 mL of a 5 mg/mL prednisolone acetate suspension, or one 5 mg tablet of a commercially available product, was administered. Blood samples were taken at determined intervals. Pharmacokinetic parameters used to evaluate and compare the relative bioavailability, and therefore bioequivalence, of the two formulations of prednisolone after a single oral dose administration under fasting conditions were $C_{max}$, $AUC_T$, $AUC_\infty$, $K_{el}$ and $T_{1/2el}$.

$C_{max}$—Maximum Concentration.

$AUC_T$—Area under the Concentration-time Curve Using the Trapezoidal Method to the Last Measurable Concentration;

$AUC_\infty$—Area under the Concentration-time Curve extrapolated to infinity;

$K_{el}$—Elimination Rate Constant;

$T_{1/2el}$—Terminal Half-Life.

Bioequivalence was determined using the 90% confidence interval for the exponential of the difference between the tablet and the suspension. The test met the 80.00-125% confidence interval limits with a statistical power of at least 80%.

TABLE 5

Bioequivalency: Prednisolone 5 mg/5 mL Suspension versus 5 mg/5 mL Syrup versus 5 mg Tablets Following a 5 mg administration/Fasting State (100% prelims N = 23/23)

| PARAMETER | Prednisolone 5 mg/ml Suspension | | Prednisolone 5 mg Tablet | |
|---|---|---|---|---|
| | MEAN | Coefficient of Variation | MEAN | Coefficient of Variation |
| $C_{max}$ (ng/mL) | 160.90 | 15.8 | 176.27 | 18.7 |
| $T_{max}$ (hours) | 1.33 | 41.6 | 1.00 | 33.2 |
| $AUC_T$ (ng · h/mL) | 821.73 | 20.2 | 812.39 | 17.7 |
| $AUC_\infty$ (ng · h/mL) | 852.23 | 19.6 | 846.53 | 17.1 |
| $K_{el}$ (hour$^{-1}$) | 0.2681 | 13.4 | 0.2629 | 9.7 |
| $T_{1/2el}$ (hours) | 2.63 | 12.6 | 2.66 | 10.0 |

For Tmax, the median is presented.

In describing embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The above-described embodiments of the invention may be modified or varied, and elements added or omitted, without departing from the invention, as appreciated by those skilled in the art in light of the above teachings. Each reference cited herein is incorporated by reference as if each were individually incorporated by reference.

The invention claimed is:

1. A pharmaceutical composition for oral delivery, comprising a pharmaceutically effective amount of prednisolone acetate particles dispersed in suspension in the composition, wherein the composition is suitable for oral delivery and wherein the prednisolone acetate has a median particle size in the range of about 1μm to about 30μm.

2. The pharmaceutical composition of claim 1, further comprising a thickening agent.

3. The pharmaceutical composition of claim 1, comprising from about 0.5 mg/mL to about 5 mg/mL of prednisolone acetate.

4. The pharmaceutical composition of claim 1, wherein the prednisolone acetate has a median particle size of about 5μm to about 20 μm.

5. The pharmaceutical composition of claim l, wherein the prednisolone acetate has a median particle size of about 6μm to about 8μm.

6. The pharmaceutical composition of claim 2 wherein the thickening agent is a carbomer.

7. The pharmaceutical composition of claim 1, further comprising a wetting agent.

8. The pharmaceutical composition of claim 2 having a pH of between about 4.0 to about 5.9.

9. The pharmaceutical composition of claim 2 having a pH of between about 4.6 to about 5.4.

10. The pharmaceutical composition of claim 1, comprising from about 0.5 mg/mL to about 5 mg/mL of prednisolone acetate, water, glycerin, sorbitol in an amount up to about 20m % (w/w), propylene glycol in an amount up to about 20% (w/w), wetting agent in an amount up to about 3% (w/w) and a thickening agent in an amount up to about 1% (w/w).

11. The pharmaceutical composition of claim 1, comprising:
   a. from about 5 mg/5 mL to about 15 mg/5 mL prednisolone acetate in suspension in the composition;
   b. 0.1% poloxamer 188;
   c. 50% glycerin;
   d. 5% sorbitol crystalline;
   e. 5% propylene glycol;
   f. 0.065% edetate disodium;
   g. 0.2% sucralose;
   h. carbomer in an amount up to about 1%;
   i. 0.04% butylparaben; and
   j. sodium hydroxide.

12. The pharmaceutical composition of claim 1, wherein the pH is between about 4.8 to about 5.2.

13. A method of treating a patient in need of prednisolone comprising the step of orally administering a therapeutically effective amount of the pharmaceutical composition of claim 1.

14. The method of claim 13 wherein the patient is suffering from a medical condition selected from the group consisting of endocrine disorders, rheumatic disorders, collagen diseases, dermatologic diseases, allergic states, respiratory diseases, hemaologic disorders, neoplastic diseases, edema, gastrointestinal diseases or nervous diseases.

15. The composition of claim 1, wherein the median particle size is below about 20μm.

16. The composition of claim 1, wherein the median particle size is below about 10μm.

17. The composition of claim 1, wherein the median particle size is below about 8μm.

18. The composition of claim 1, wherein the prednisolone acetate particles stay within the median particle size range over time.

19. The pharmaceutical composition of claim 1, wherein a 5 mg dose of the composition, when administered to a human, is bioequivalent, within the 80-125% confidence interval and with a statistical power of at least 80%, to a 5 mg tablet of prednisolone.

20. The pharmaceutical composition of claim 1, wherein the composition exhibits an in vitro dissolution profile of about 85% released after about 15 minutes, about 95% released after about 30 minutes, about 97% released after about 45 minutes and about 97% released after about 60 m minutes.

21. The pharmaceutical composition of claim 1, wherein the prednisolone acetate remains dispersed in the suspension without agitation during the shelf life of the composition.

22. The pharmaceutical composition of claim 1, comprising carbomer and poloxamer.

23. A pharmaceutical composition for oral delivery comprising a pharmaceutically effective amount of micronized prednisolone acetate particles in suspension in the composition, wherein the composition, when administered to humans and tested for one or more pharmacokinetic parameters selected from the group consisting of $C_{max}$, $T_{max}$, $AUC_T$, $AUC_\infty$, $K_{el}$, and $T_{1/2\ el}$, is bioequivalent to a 5 mg tablet of prednisolone, within the 80-125% confidence interval and with a statistical power of at least 80%, and wherein the composition is suitable for oral delivery and wherein the prednisolone acetate has a median particle size in the range of about 1 μm to about 30 μm.

24. The pharmaceutical composition of claim 23, wherein the composition has pharmacokinetic parameters within the 80-125% confidence interval, with a statistical power of at least 80%, of one or more of the following values:
 a. $C_{max}$ of 176.27 ng/mL;
 b. $T_{max}$ of 1.00 hour;
 c. $AUC_T$ of 812.39 ng·h/mL;
 d. $AUC_\infty$ of 846.53 ng·h/mL;
 e. $K_{el}$ of 0.2629 hr$^{-1}$; and
 f. $T_{1/2\ el}$ of 2.66 hours.

25. A pharmaceutical composition comprising a pharmaceutically effective amount of prednisolone acetate particles dispersed in suspension in the composition, wherein the composition is suitable for oral delivery, comprises components that are mutually compatible, comprises carbomer and a wetting agent, has a pH between about 4.0 and 5.9, is palatable, has a viscosity of about 5,000 to about 15,000 cps, and is storage stable.

26. The composition of claim 25, wherein the pH is between about 4.6 and about 5.4.

27. The composition of claim 25, wherein the pH is between about 5 and about 5.4.

28. The composition of claim 25, wherein the wetting agent is poloxamer.

29. The composition of claim 25, wherein the composition comprises an aqueous vehicle.

30. The pharmaceutical composition of claim 25, wherein the prednisolone acetate remains dispersed in the suspension without agitation during the shelf life of the composition and has a crystalline stability such that the prednisolone particles stay within a target particle size range over time.

31. The pharmaceutical composition of claim 25, wherein the composition is spill-resistant.

32. A pharmaceutical composition comprising a pharmaceutically effective amount of fine milled prednisolone acetate particles in suspension in a vehicle, wherein the composition exhibits an in vitro dissolution profile of about 45% released after about 5 minutes, about 85% released after about 15 minutes, about 95% released after about 30 minutes, about 97% released after about 45 minutes and about 97% released after about 60 minutes, wherein the composition is suitable for oral delivery and comprises carbomer and a wetting agent, and has a pH between about 4.0 and 5.9.

\* \* \* \* \*

UNITED STATES PATENT AND TRADEMARK OFFICE
CERTIFICATE OF CORRECTION

| | | |
|---|---|---|
| PATENT NO. | : 7,799,331 B2 | Page 1 of 1 |
| APPLICATION NO. | : 11/457197 | |
| DATED | : September 21, 2010 | |
| INVENTOR(S) | : Asotra et al. | |

It is certified that error appears in the above-identified patent and that said Letters Patent is hereby corrected as shown below:

On the Title Page

Under the subheading "Item (75) Inventors," at line 2, replace ~~Botton~~ with Bolton.

In Claim 10, at column 8, line 36, replace ~~20m%~~ with 20%.

Signed and Sealed this
Fourth Day of January, 2011

David J. Kappos
*Director of the United States Patent and Trademark Office*